(12) United States Patent
Pienknagura

(10) Patent No.: US 7,247,166 B2
(45) Date of Patent: Jul. 24, 2007

(54) INTRAVASCULAR STENT WITH EXTENDIBLE END RINGS

(75) Inventor: Carla Rosa Pienknagura, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 520 days.

(21) Appl. No.: 10/675,610

(22) Filed: Sep. 29, 2003

(65) Prior Publication Data

US 2005/0070991 A1    Mar. 31, 2005

(51) Int. Cl.
*A61F 2/06* (2006.01)
*A61M 29/02* (2006.01)

(52) U.S. Cl. .................. 623/1.15; 604/96.01; 606/198

(58) Field of Classification Search ...... 623/1.11–1.54; 606/194

See application file for complete search history.

(56) References Cited

U.S. PATENT DOCUMENTS

| | | | |
|---|---|---|---|
| 5,695,516 A | * | 12/1997 | Fischell et al. ............. 606/194 |
| 5,755,776 A | * | 5/1998 | Al-Saadon ................. 623/1.15 |
| 6,190,405 B1 | | 2/2001 | Culombo et al. |
| 6,287,336 B1 | | 9/2001 | Globerman et al. |
| 6,334,871 B1 | | 1/2002 | Dor et al. |
| 6,440,162 B1 | | 8/2002 | Cox et al. |
| 6,652,579 B1 | | 11/2003 | Cox et al. |
| 6,679,911 B2 | * | 1/2004 | Burgermeister ............ 623/1.15 |
| 2003/0105515 A1 | | 6/2003 | Skubitz et al. |
| 2004/0024445 A1 | | 2/2004 | Dickson |

OTHER PUBLICATIONS

U.S. Appl. No. 08/881,059, filed Jun. 24, 1997, abandoned Oct. 10, 2001.

* cited by examiner

*Primary Examiner*—Glenn K. Dawson
(74) *Attorney, Agent, or Firm*—Fulwider Patton LLP

(57) ABSTRACT

An expandable stent for implanting in a body lumen, such as a coronary artery, peripheral artery, or other body lumen includes cylindrical rings connected by undulating links. The stent has a high degree of flexibility in the longitudinal direction, yet has adequate vessel wall coverage and radial strength sufficient to hold open an artery or other body lumen. The distal and proximal end ring have peaks that extend longitudinally when the stent is radially expanded. The end ring extensions reduce the likelihood of the development of peri-stent restenosis.

30 Claims, 10 Drawing Sheets

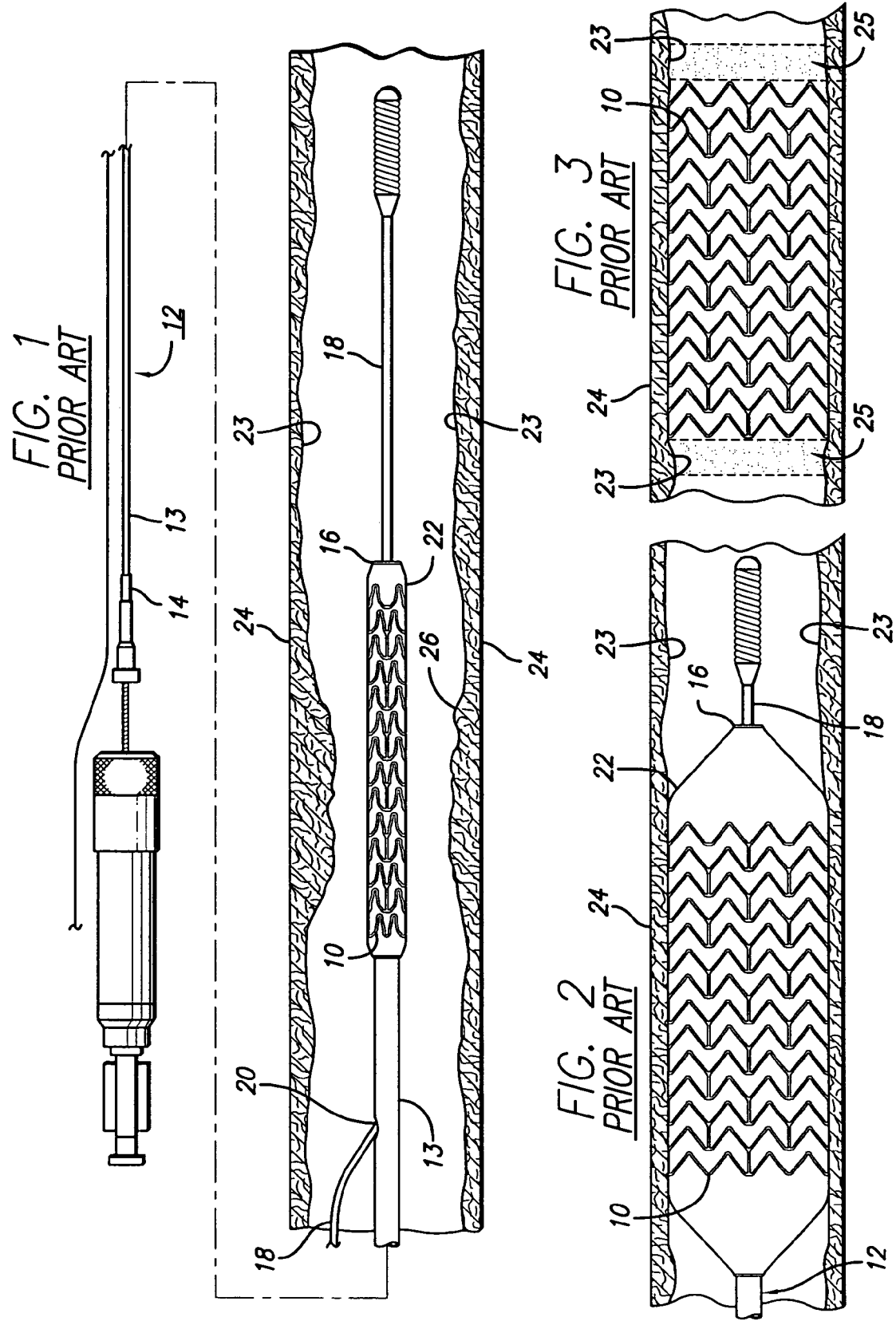

INTRAVASCULAR STENT WITH EXTENDIBLE END RINGS

BACKGROUND OF THE INVENTION

The invention relates to vascular repair devices, and in particular intravascular stents, which are adapted to be implanted into a patient's body lumen, such as a blood vessel or coronary artery, to maintain the patency thereof. Stents are particularly useful in the treatment of atherosclerotic stenosis in arteries and blood vessels.

Stents are generally tubular-shaped devices which function to hold open a segment of a blood vessel or other body lumen such as a coronary artery. They also are suitable for use to support and hold back a dissected arterial lining that can occlude the fluid passageway. At present, there are numerous commercial stents being marketed throughout the world. For example, the prior art stents depicted in FIGS. 1-5 have multiple cylindrical rings connected by one or more undulating links. While some of these stents are flexible and have the appropriate radial rigidity needed to hold open a vessel or artery, there typically is a tradeoff between flexibility and radial strength and the ability to tightly compress or crimp the stent onto a catheter so that it does not move relative to the catheter or dislodge prematurely prior to controlled implantation in a vessel.

Presently, there is substantial development of drug coated stents, particularly in the coronary arteries, to reduce the likelihood of the development of restenosis after the stent has been implanted. One problem being encountered with a stent, including these drug coated stents, is that restenosis can sometimes occur at the stent ends, both distally and proximally of the implanted stent. The development of restenosis at the stent ends is sometimes referred to as peri-stent restenosis. While various theories exist as to the reasons for the development of restenosis at the stent ends, one important factor appears to be injury to the arterial wall by the non-working length of the balloon. In other words, that portion of the balloon that extends beyond the stent will expand into the arterial wall and cause stretching or other injury that will eventually lead to the development of restenosis. The drug coating on the stent will release the drug substantially in the area where the stent contacts the arterial wall, leaving the distal and proximal areas beyond the stent untreated with the therapeutic drug. As a result, the likelihood of the development of restenosis beyond the ends of the stent is much greater since the therapeutic drug does not treat that injured area.

SUMMARY OF THE INVENTION

The present invention is directed to an intravascular stent that has a pattern or configuration that permits one or more end rings to extend longitudinally as the stent is expanded radially. The extension of the end rings in the longitudinal direction will permit drug delivery from a drug coating on the end rings to extend beyond the balloon working length. By delivering a therapeutic drug beyond the balloon working length, the drug coated stent and end rings will reduce the likelihood of the development of peri-stent restenosis. The stent also is highly flexible along its longitudinal axis to facilitate delivery through tortuous body lumens, but which is stiff and stable enough radially in its expanded condition to maintain the patency of a body lumen such as an artery when the stent is implanted therein.

The stent of the present invention generally includes a plurality of cylindrical rings that are interconnected to form the stent. The stent typically is mounted on a balloon catheter if it is balloon expandable or mounted on or in a catheter without a balloon if it is self-expanding. Typically, the balloon portion of the catheter has a working length which is that portion of the balloon that expands into contact with a body lumen, such as a coronary artery. The balloon shoulder is that portion of the balloon that transitions from the working length to the balloon taper. When a stent is mounted on the balloon, the stent-to-shoulder distance is the distance between the stent ends and the balloon shoulder.

In one embodiment, each of the cylindrical rings making up the stent have a proximal end and a distal end and a cylindrical plane defined by a cylindrical outer wall surface that extends circumferentially between the proximal end and the distal end of the cylindrical ring. Generally the cylindrical rings have a serpentine or undulating shape which includes at least one U-shaped element, and typically each ring has more than one U-shaped element. Importantly, the cylindrical rings having a serpentine or undulating shape are radially expandable outwardly so that as the stent expands (either by balloon expansion or because the stent is self-expanding) the serpentine or undulating shape spreads apart. In accordance with the invention, the end rings of the stent have a double curved portion that not only expands radially outwardly and thereby spreading apart the bends or curves, but the end rings also extend longitudinally during expansion. For example, at least a portion of the distal end ring extends distally in the longitudinal direction and at least a portion of the proximal end ring extends proximally in a longitudinal direction upon expansion of the stent and the end rings. More specifically, the distal end ring has a first peak and a second peak and the proximal end ring has a first peak and a second peak and upon expansion of the end ring, the first peak leverages off of the expansion of the end ring so that as the first peak expands, the second peak also expands and leverages off of the ending expansion and the first peak expansion and is deformed away from the first peak in a longitudinal direction. When the stent of the invention is drug coated, the longitudinal extension of the second peak provides a therapeutic drug to the peri-stent area that was previously untreated by prior art stents, that is, the area that is beyond the working length of the expanded balloon.

In one embodiment, the distal end ring and the proximal end ring have undulations or U-shaped members that expand radially outwardly when the stent is expanded. These U-shaped members have first peaks that have a radius of curvature that can be uniform or irregular. Second peaks extend from the first peaks so that an aperture is formed by the peaks. When the stent is expanded the second peaks expand and are leveraged in a longitudinal direction by the opening of the U-shaped member and by the expansion of the first peaks. The distance that the second peaks extend in the longitudinal direction can be substantial and is a function of numerous factors such as the amount of radial expansion of the stent, the radius of curvature of the first and second peaks, the radial thickness and the width of the struts in peaks, and the structural relationship between the first peaks and the second peaks. One measure of the longitudinal extension of the end rings is the stent-to-shoulder distance (STS). When the stent is mounted on a balloon and crimped tightly, the distance from the stent proximal end to the balloon shoulder (STS) and the distance from the stent distal end to the stent shoulder (STS) represents a distance A, for example +0.2 mm. After stent expansion and after the distal and proximal ends extend longitudinally, the STS is distance B, for example, −0.4 mm. The negative 0.4 mm means that the second peaks extend beyond the balloon shoulder into the so-called peri-stent area.

In one embodiment, the cylindrical rings are interconnected by at least one undulating link which attaches one cylindrical ring to an adjacent cylindrical ring. The undulating links are highly flexible and allow the stent to be highly flexible along its longitudinal axis. At least some of the undulating links have a curved portion that extends transverse to the stent longitudinal axis for a predetermined distance that coincides with one of the U-shaped elements. More specifically, the curved portion extends in a transverse manner such that it would intersect with the corresponding U-shaped element, however, the corresponding U-shaped element is shorter in length than other U-shaped elements in the same ring. Thus, when the stent is compressed or crimped onto the catheter, the curved portions do not overlap or intersect with the adjacent U-shaped element since that element is shorter in length than similar U-shaped elements in the particular ring. In this manner, the stent can be compressed or crimped to a much tighter or smaller diameter onto the catheter which permits low profile delivery as well as a tight gripping force on the catheter to reduce the likelihood of movement between the stent and the catheter during delivery and prior to implanting the stent in the vessel.

The undulating links may take various configurations but in general have an undulating or serpentine shape. The undulating links can include bends connected by substantially straight portions wherein the substantially straight portions are substantially perpendicular to the stent longitudinal axis.

Not only do the undulating links that interconnect the cylindrical rings provide flexibility to the stent, but the positioning of the links also enhances the flexibility by allowing uniform flexibility when the stent is bent in any direction along its longitudinal axis. Uniform flexibility along the stent derives in part from the links of one ring being circumferentially offset from the links in an adjacent ring. Further, the cylindrical rings are configured to provide flexibility to the stent in that portions of the rings can flex or bend and tip outwardly as the stent is delivered through a tortuous vessel.

The cylindrical rings typically are formed of a plurality of peaks and valleys, where the valleys of one cylindrical ring are circumferentially offset from the valleys of an adjacent cylindrical ring. In this configuration, at least one undulating link attaches each cylindrical ring to an adjacent cylindrical ring so that at least a portion of the undulating links is positioned within one of the valleys and it attaches the valley to an adjacent peak.

While the cylindrical rings and undulating links generally are not separate structures, they have been conveniently referred to as rings and links for ease of identification. Further, the cylindrical rings can be thought of as comprising a series of U's, W's and Y-shaped structures in a repeating pattern. Again, while the cylindrical rings are not divided up or segmented into U's, W's and Y's, the pattern of the cylindrical rings resemble such configuration. The U's, W's and Y's promote flexibility in the stent primarily by flexing and by tipping radially outwardly as the stent is delivered through a tortuous vessel.

The undulating links are positioned so that the curved portion of the link is outside the curved part of the W-shaped portion. Since the curved portion does not substantially expand (if at all) when the stent is expanded, it will continue to provide good vessel wall coverage even as the curved part of the W-shaped portion spreads apart as the stent is expanded. The curved portion of the link extends in a direction transverse to the stent longitudinal axis for a distance that positions it adjacent and proximal to the peak of a U-shaped element. These U-shaped elements have struts that are shorter than the struts of the other U-shaped elements in the same cylindrical ring so that as the stent is compressed the curved portion of the link does not overlap the adjacent U-shaped element.

In one embodiment, the W-shaped portion has a first and second radius at its base where the first radius is greater than the second radius so that the first radius expands more easily than the second radius when the stent is expanded. The first radius corresponds with a second peak (U-shaped member) which is shorter than the other peaks in the ring. The second peak has shorter struts than the struts of the other peaks and as a result expands more slowly when the stent expands. Thus, faster expansion rate of the first radius of the W-shaped portion has a tendency to compensate for the slower expansion rate of the adjacent shorter second peak to provide overall uniform expansion of the stent. Also, the shorter second peak can have a greater radius than the longer first peaks, again to provide different expansion rates to obtain more uniform stent expansion.

The number and location of undulating links that interconnect adjacent cylindrical rings can be varied as the application requires. Since the undulating links typically do not expand when the cylindrical rings of the stent expand radially outwardly, the links are free to continue to provide flexibility and to also provide a scaffolding function to assist in holding open the artery. Importantly, the addition or removal of the undulating links has very little impact on the overall longitudinal flexibility of the stent. Each undulating link is configured so that it promotes flexibility whereas some prior art connectors actually reduce flexibility of the stent.

The cylindrical rings of the stent are plastically deformed when expanded when the stent is made from a metal that is balloon expandable. Typically, the balloon-expandable stent is made from a stainless steel alloy, cobalt-chromium alloy, titanium, tantalum, or similar materials.

In one embodiment, the cylindrical rings of the stent expand radially outwardly when the stent is formed from superelastic alloys, such as nickel-titanium (NiTi) alloys. In the case of superelastic alloys, the stent expands upon application of a temperature change or when a stress is relieved, as in the case of a pseudoelastic phase change. As with balloon-expandable stents, stents formed from superelastic alloys of the present invention have end rings that extend longitudinally when expanded. Both the proximal and distal end rings have first peaks and second peaks that provide for the second peaks to extend longitudinally as the superelastic alloy stent expands. After the stent self-expands, a balloon catheter may be used to further expand and implant the stent in an artery or other body lumen.

Because of the undulating configuration of the links, the stent has a high degree of flexibility along the stent axis, which reduces the tendency of stent fishscaling. Stent fishscaling can occur when the stent is bent and portions of the stent project outward when the stent is in the unexpanded condition. The present invention undulating links reduce the likelihood of fishscaling.

Further, because of the positioning of the links, and the fact that the links do not expand or stretch when the stent is radially expanded, the overall length of the stent is substantially the same in the unexpanded and expanded configurations. In other words, the stent will not substantially shorten upon expansion. The end rings of course extend longitudinally as described, however, the distance the end rings extend is small compared to the overall length of the stent. By way of example only, a stent that is 20.3 mm before expansion, will be about 21.1 mm after expansion, the increase in length due entirely to the lengthening of the distal and proximal end rings.

The stent may be formed from a tube by laser cutting the pattern of cylindrical rings and undulating links in the tube. The stent also may be formed by laser cutting a flat metal sheet in the pattern of the cylindrical rings and links, and then rolling the pattern into the shape of the tubular stent and providing a longitudinal weld to form the stent.

BRIEF DESCRIPTION OF THE DRAWINGS

FIG. 1 is an elevational view, partially in section, of a prior art stent mounted on a rapid-exchange delivery catheter and positioned within an artery.

FIG. 2 is an elevational view, partially in section, similar to the stent shown in FIG. 1 wherein the prior art stent is expanded within the artery, so that it embeds within the arterial wall.

FIG. 3 is an elevational view, partially in section, showing the expanded prior art stent implanted within the artery after withdrawal of the rapid-exchange delivery catheter.

DETAILED DESCRIPTION OF THE PREFERRED EMBODIMENTS

Figure 4:
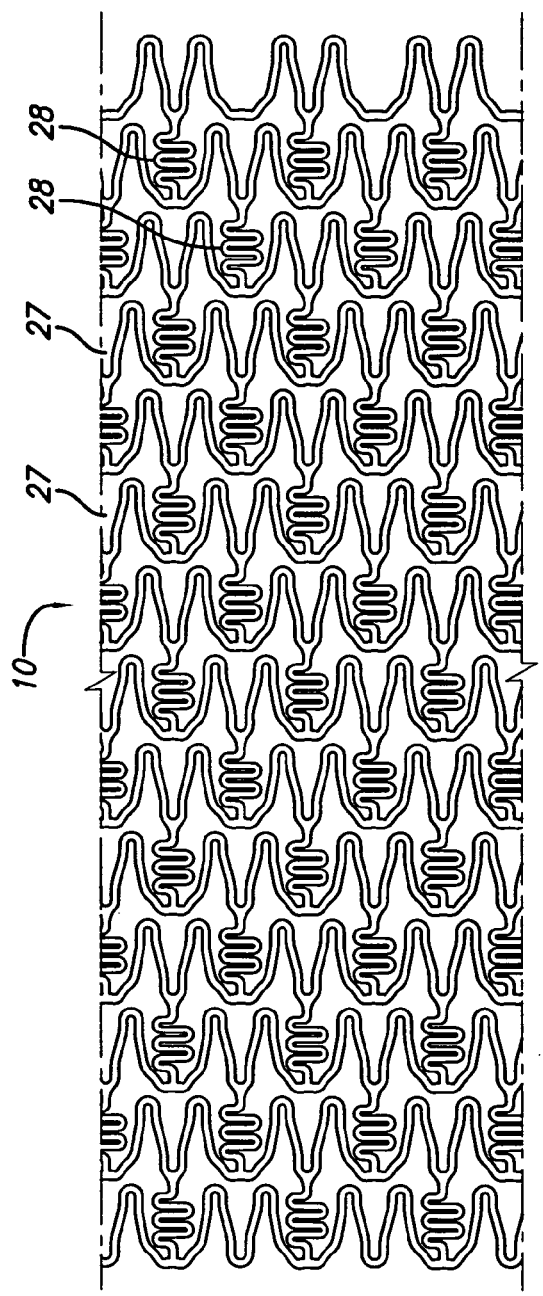
FIG. 4 is a plan view of a flattened prior art stent which illustrates the pattern of the stent shown in FIGS. 1-3.

The present invention stent improves on existing stents by providing a longitudinally flexible stent having a uniquely designed pattern of expandable cylindrical rings with stent end rings that lengthen as the rings expand radially outwardly. A distal end ring lengthens distally in a longitudinal direction and a proximal end ring extends and lengthens longitudinally in the proximal direction as the stent expands due to the unique and novel twin peak design. The stent can be drug coated so that the therapeutic drug is delivered by the extended end rings to reduce the likelihood of the development of peri-stent restenosis. In addition to providing longitudinal flexibility, the stent of the present invention also provides radial rigidity and a high degree of scaffolding of a vessel wall, such as a coronary artery.

Turning to the drawings, FIG. 1 depicts a prior art stent 10 mounted on a conventional catheter assembly 12 which is used to deliver the stent and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well known methods of an over the wire system (not shown) or a well known rapid exchange catheter system, such as the one shown in FIG. 1.

Catheter assembly 12 as depicted in FIG. 1 is of the well known rapid exchange type which includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque that has been previously treated by angioplasty or another repair procedure. Stent 10 is used to repair a diseased or damaged arterial wall which may include the plaque 26 (which can include vulnerable plaque) as shown in FIG. 1, or a dissection, or a flap which are sometimes found in the coronary arteries, peripheral arteries and other vessels.

In a typical procedure to implant prior art stent 10, the guide wire 18 is advanced through the patient's vascular system by well known methods so that the distal end of the guide wire is advanced past the plaque or diseased area 26. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the prior art stent expanded and pressed against the vessel wall, and in FIG. 3, the implanted stent remains in the vessel after the balloon has been deflated and the catheter assembly and guide wire have been withdrawn from the patient.

The prior art stent 10 serves to hold open the artery after the catheter is withdrawn, as illustrated by FIG. 3. Due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with endothelial cell growth which further minimizes blood flow interference. The undulating portion of the stent provides good tacking characteristics to prevent stent movement within the artery. Furthermore, the closely spaced cylindrical elements at regular intervals provide uniform support for the wall of the artery, and consequently are well adapted to tack up and hold in place small flaps or dissections in the wall of the artery, as illustrated in FIGS. 2 and 3.

Figure 5:
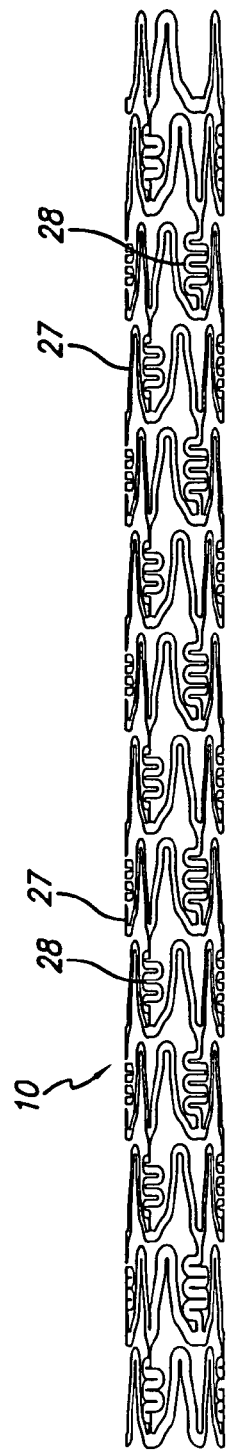
FIG. 5 is a side view of the prior art stent of FIG. 4 in a cylindrical configuration and in an unexpanded state.

One of the problems associated with some prior art stents 10, such as the one shown in FIGS. 4 and 5, is that the pattern of rings 27 and links 28 are essentially the same throughout the stent. Further, such prior art stents may have a tendency to foreshorten between one and three percent of the overall length of the stent during expansion, depending upon the diameter to which the stent is expanded. If a stent foreshortens when it is expanded, it will compound the problem of peri-stent restenosis since the stent-to-shoulder (STS) distance will increase as the stent is expanded and as it foreshortens while it is still on the balloon and expanding into contact with the lumen or artery. In other words, as the prior art stents continue to expand and foreshorten, the STS distance increases and more of the working length of the balloon 22 contacts the vessel wall thereby imparting injury as the vessel wall expands under the expanding pressure of the balloon. This is best illustrated by reference to FIG. 3 showing the peri-stent area 25 that results from the expansion of the working portion of the balloon expanding into contact with the vessel wall 23. The present invention overcomes the problems of the prior art stents foreshortening and the STS distance of the balloon increasing and causing a peri-stent restenosis problem.

In keeping with the present invention, FIGS. 6-14 depict stent 30 in various configurations. Referring to FIG. 6A, for example stent 30 is shown in a flattened condition so that the pattern can be clearly viewed, even though the stent is in a cylindrical form in use, such as shown in FIG. 6C. The stent is typically formed from a tubular member, however, it can be formed from a flat sheet such as shown in FIG. 6A and rolled into a cylindrical configuration as shown in FIG. 6C.

Figure 6A:
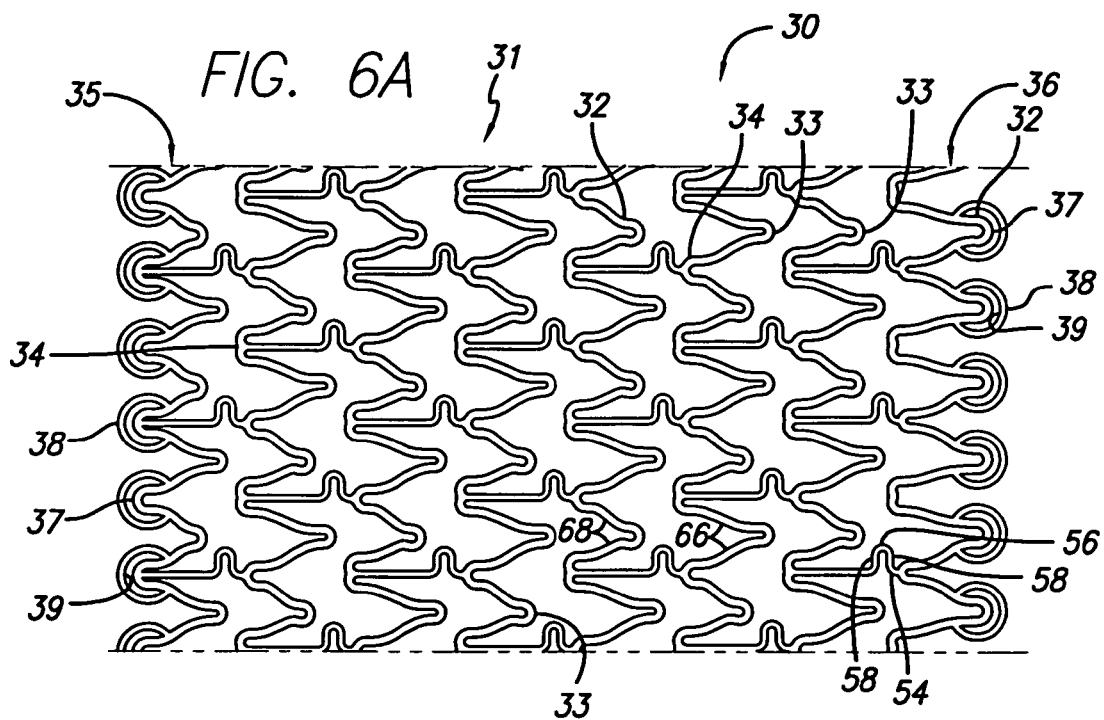
FIG. 6A is a plan view of a flattened stent of one embodiment of the invention which illustrates the pattern of the rings and links, including the end rings.
Figure 6B:
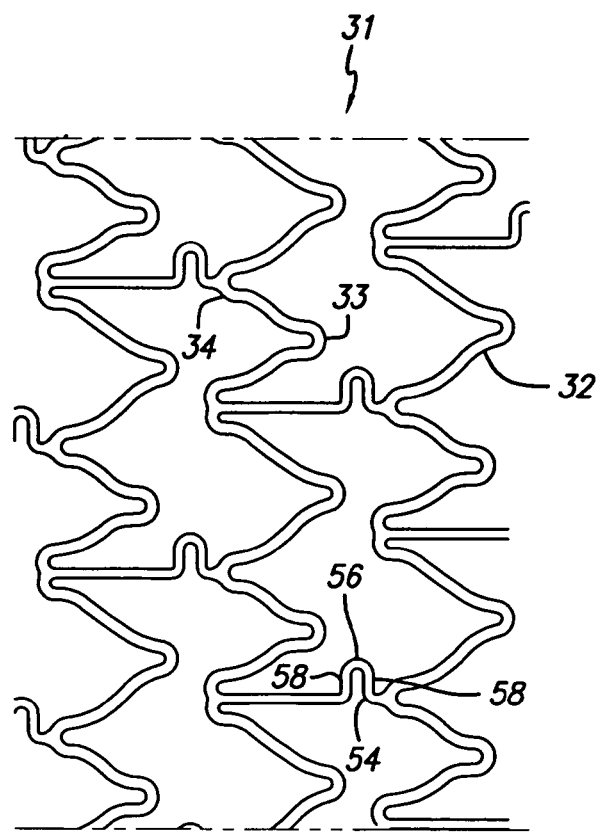
FIG. 6B is a partial plan view of the stent of FIG. 6A which has been expanded.
Figure 6C:
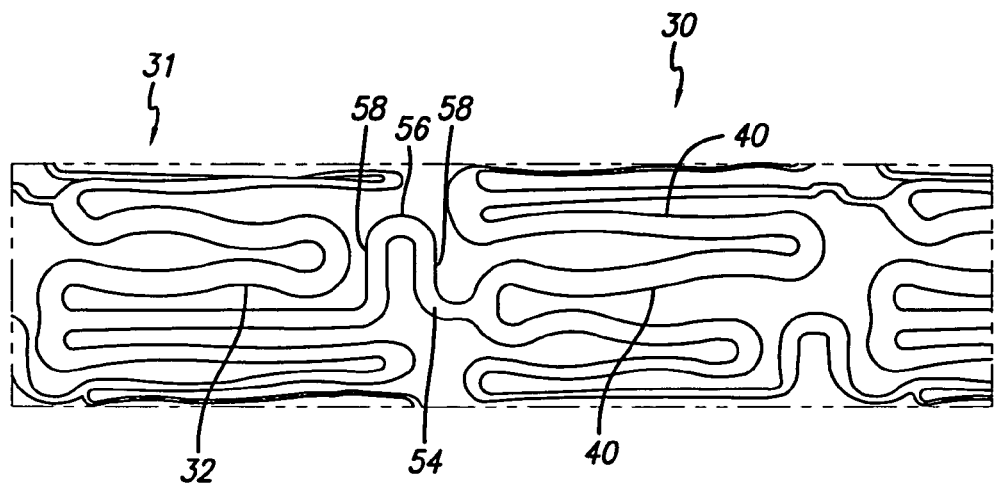
FIG. 6C is a plan view of a portion of the stent of FIG. 6A rolled into a cylindrical configuration and tightly crimped.
Figure 7A:
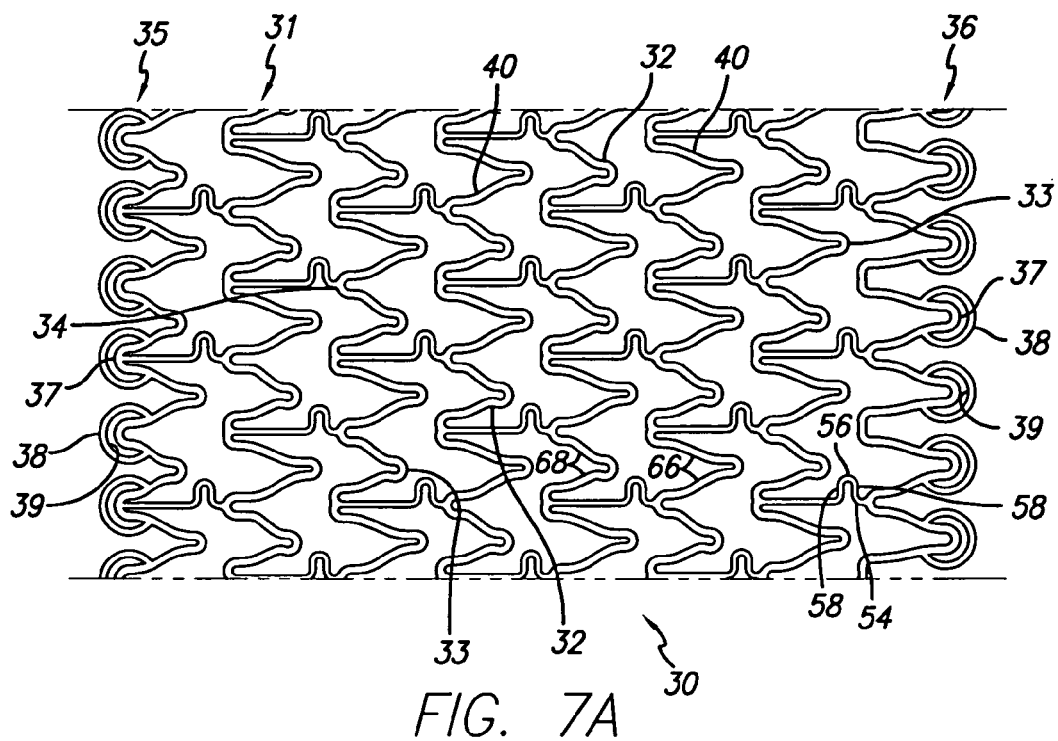
FIG. 7A is a plan view of a flattened stent of another embodiment of the invention which illustrates the pattern of the rings and links and a distal end ring and a proximal end ring.
Figure 7B:
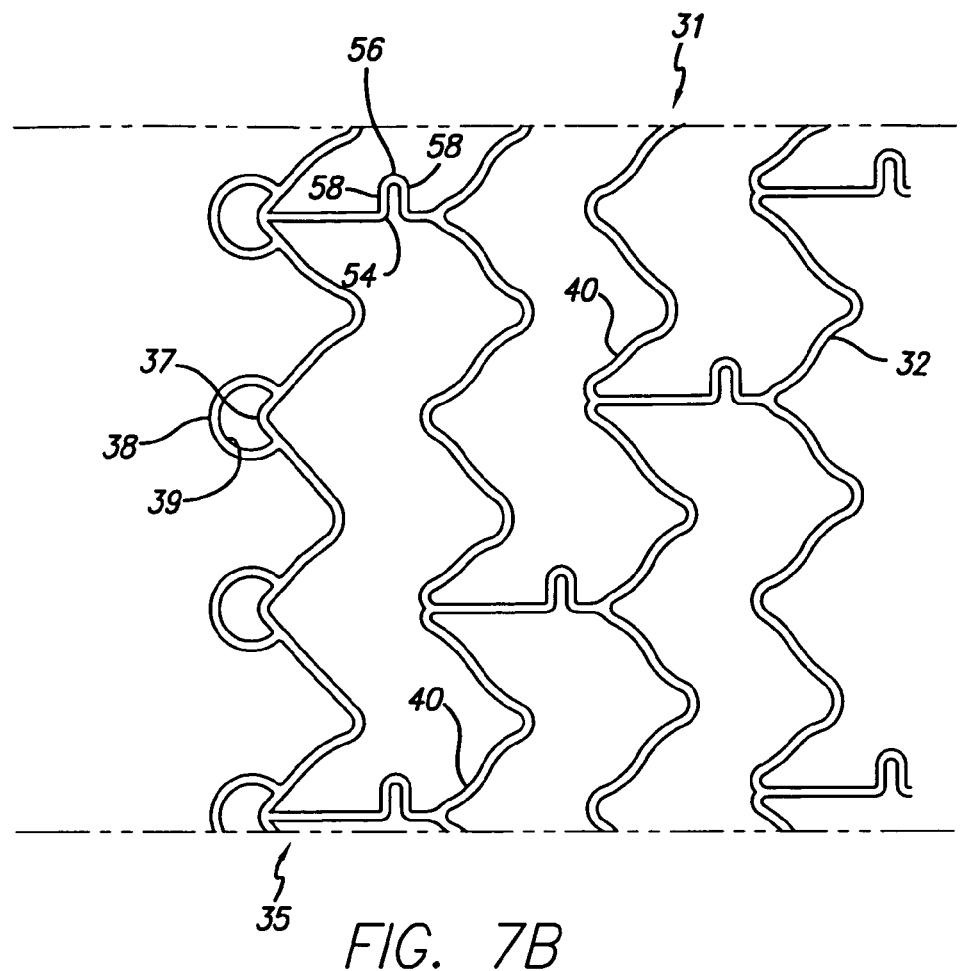
FIG. 7B is a partial plan view of the stent of FIG. 7A which has been expanded.
Figure 7C:
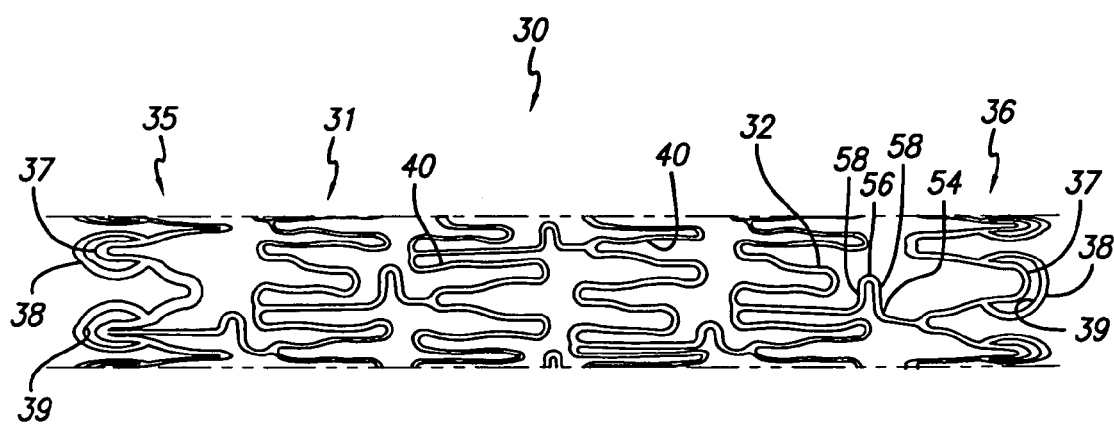
FIG. 7C is a portion of the stent of FIG. 7A that is illustrated in a cylindrical configuration and is tightly crimped or compressed.
Figure 8:
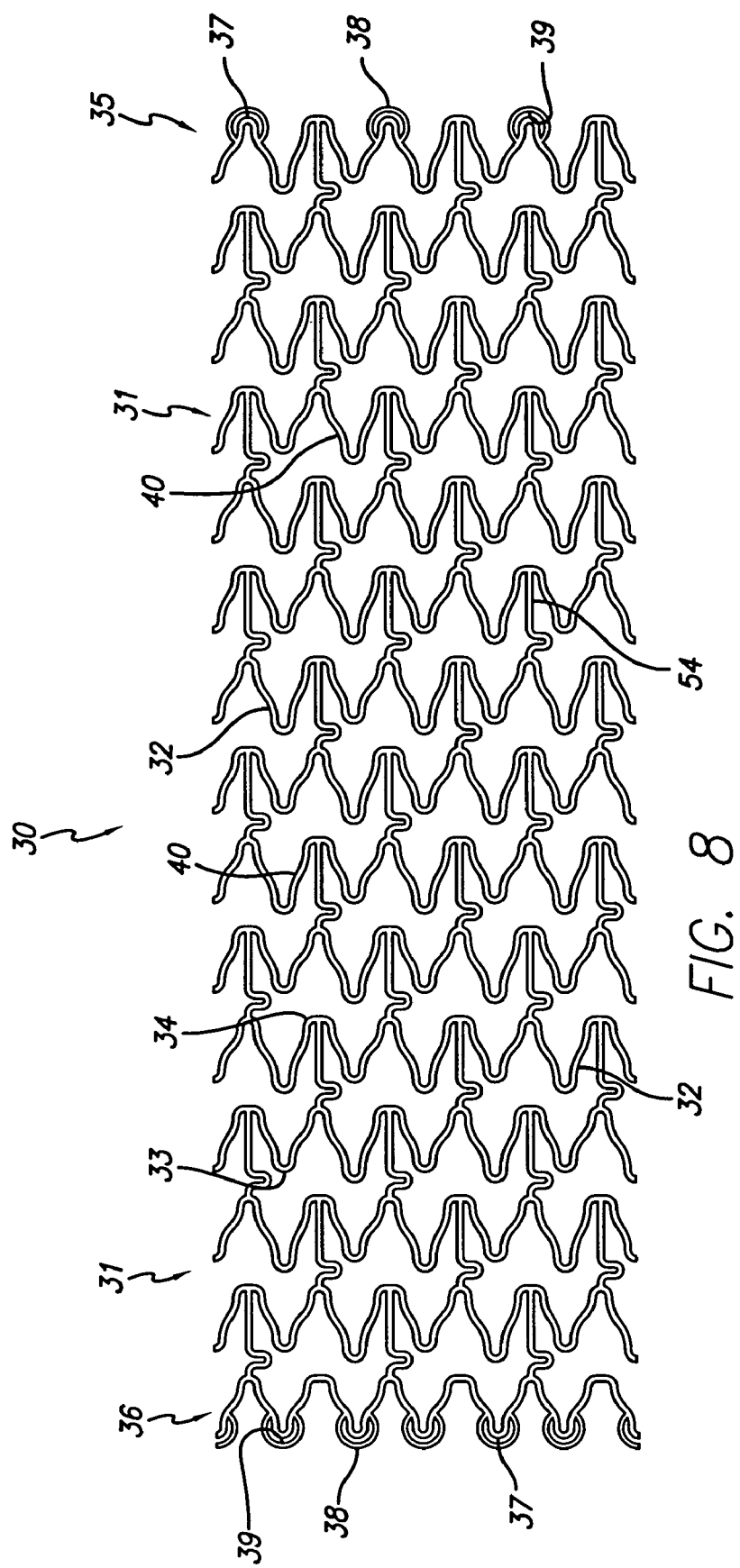
FIG. 8 is a plan view of a flattened stent depicting one embodiment of the invention illustrating the end rings prior to full expansion.

As shown in FIGS. 6-8, stent 30 is made up of cylindrical rings 31 which extend circumferentially around the stent when it is in a tubular form (see FIGS. 6C and 7C). The stent has a delivery diameter as shown in FIG. 7C, and an implanted diameter as shown in FIG. 7B. Each cylindrical ring has a cylindrical ring proximal end 33 and a cylindrical ring distal end 34. Typically, since the stent is laser cut from a tube there are no discreet parts such as the described cylindrical rings and links. However, it is beneficial for identification and reference to various parts to refer to the cylindrical rings and links and other parts of the stent as follows.

In keeping with the invention, and as shown in FIGS. 6 and 7, stent 30 includes cylindrical rings 31 that are aligned along a common longitudinal axis and in this embodiment, have an in-phase relationship. In this embodiment, the cylindrical rings are formed by undulations and include U-shaped members 32. Each cylindrical ring has a proximal end 33 and a distal end 34 which define the length of the cylindrical ring both in the compressed or crimped diameter (the delivery diameter) and the implanted diameter (expanded) when the stent is implanted in a vessel such as a coronary artery. In the embodiments shown in FIGS. 6 and 7, except for the cylindrical rings at the ends of the stent, all of the cylindrical rings have substantially the same patterns of undulations connected by links. The stent has a distal end ring 35 and a proximal end ring 36 that both have a different configuration or pattern than the other cylindrical rings 31. Both the distal end ring and the proximal end ring have a first peak 37 and a second peak 38 with an aperture 39 between the first peak and the second peak. When the stent expands from the delivery diameter to the expanded diameter, bar arms 40 that are connected to the first peaks spread apart which causes the first peak and the second peak to both expand circumferentially, and with respect to the second peak 38, it expands circumferentially and it extends longitudinally along the stent longitudinal axis. The bar arms should be adequately rigid or stiff so that they do not bend appreciably when the stent is expanded so that the first and second peaks will spread open rather than the bar arm bending at the intersection with the first and second peaks.

Figure 9A:
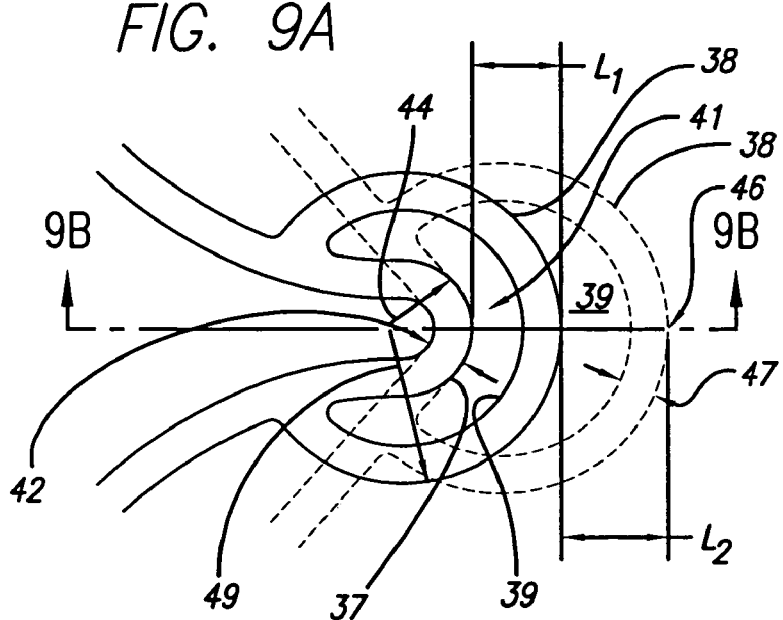
FIG. 9A is an enlarged view of a portion of an end ring, and more specifically showing the first peak and the second peak before and after the stent is expanded.

Numerous structural features dictate the relationship between the first peak 37 and the second peak 38 of the distal end ring 35 and proximal end ring 36 respectively when the stent is expanded. The first peak has an apex 41 as shown in FIGS. 9-10 and has a strut width 42 and a strut radial thickness 43. The radius of the first peak and the variability of the strut width and radial thickness are some of the structural features affecting the relationship between the first peak and the second peak during stent expansion. As shown in FIGS. 9-10, the first peak also has a crimped radius of curvature 44. In order to achieve uniform expansion, the structural relationship between the first peak and the second peak should be optimized. Accordingly, the second peak also has an apex 46 at the tip of the bend portion, a strut width 47 and a strut radial thickness 48, all of which can be varied in order to vary the radial expansion of the second peak and the extension of the second peak in the longitudinal direction. The second peak also has a crimped radius of curvature 49. When the stent expands from the crimped or delivered diameter to the expanded or implanted diameter, the circumferential expansion of the first peak will leverage the expansion both circumferentially and longitudinally of the second peak, as shown in FIGS. 9A and 10. In other words, as the first peak 37 expands, it pushes the second peak 38 longitudinally away from the body of the stent. Thus, with respect to the distal end ring 35, as the first peak expands radially outwardly and circumferentially, it leverages or pushes the second peak longitudinally in a distal direction away from the stent. Similarly, with respect to the proximal end ring 36, the first peak expands radially outwardly and circumferentially and in doing so, leverages and pushes the second peak in a proximal direction away from the stent. After the stent is expanded, the first peak expanded radius of curvature is greater than the first peak crimped radius of curvature. Likewise, the second peak expanded radius of curvature is greater than the second peak crimped radius of curvature. As shown in FIG. 9A, prior to expansion of the stent, the distances between the first and second peaks of the distal end ring and the proximal end ring is a first length L1. After the stent has been expanded to its implanted diameter, the distance between the first and second peaks of the distal end ring and the proximal end ring increases to a second length L2. In one important aspect of the invention, L2 is greater than L1 since the second peak extends longitudinally along the stent longitudinal axis upon expansion.

Figure 9B:
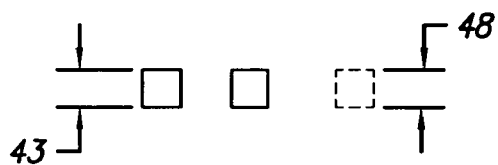
FIG. 9B is a cross-sectional view taken along line 9B-9B of the portion of the end ring shown in FIG. 9A, wherein the radial thickness of the first and second peak is shown.
Figure 10:
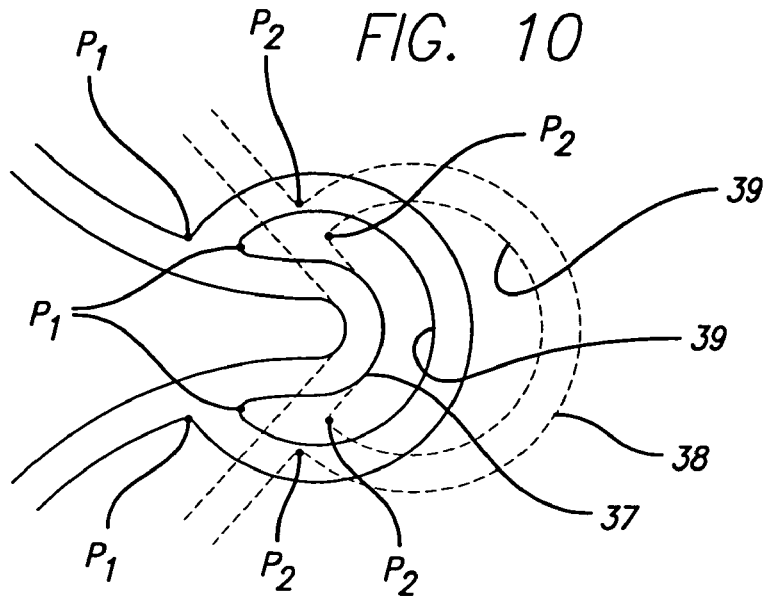
FIG. 10 is an enlarged view of a portion of an end ring, more specifically depicting the first and second peak in the unexpanded and expanded configurations.

In further keeping with the invention, and as shown in FIGS. 9A-10, various factors will contribute to the longitudinal extension of the end rings 33,34 upon expansion of the stent 30 from the first delivery diameter to the second implanted diameter. Some of these factors include the width of the various struts making up the first peak 37 and the second peak 38, as well as the radial thickness of the struts. For example, the strut width 42 of first peak 37 is wider than the strut width 47 of second peak 38. As the stent expands, the strut width 47 of the second peak will offer less resistance to expansion since it has less mass and is narrower than strut width 42 of the first peak. Similarly, the resistance to radial expansion will be affected by the radial thickness of the struts, as shown in FIG. 9B. The strut radial thickness 43 of the first peak is the same as the strut radial thickness 48 of the second peak. However, it may be advantageous to vary the strut radial thickness 43,48 of the first and second peaks to alter the expansion characteristics, and hence the extendability of the second peak along the longitudinal axis of the stent. For example, if the strut radial thickness 48 of the second peak were lessh than the strut radial thickness 43 of the first peak, there would be less resistance to expansion and thereby the second peak should expand more easily both circumferentially and extend longitudinally along the stent axis. Thus, both the strut width and the strut radial thickness in the first and second peaks are factors that contribute to the radial expansion and the extension of the second peak in a longitudinal direction.

Figure 11:
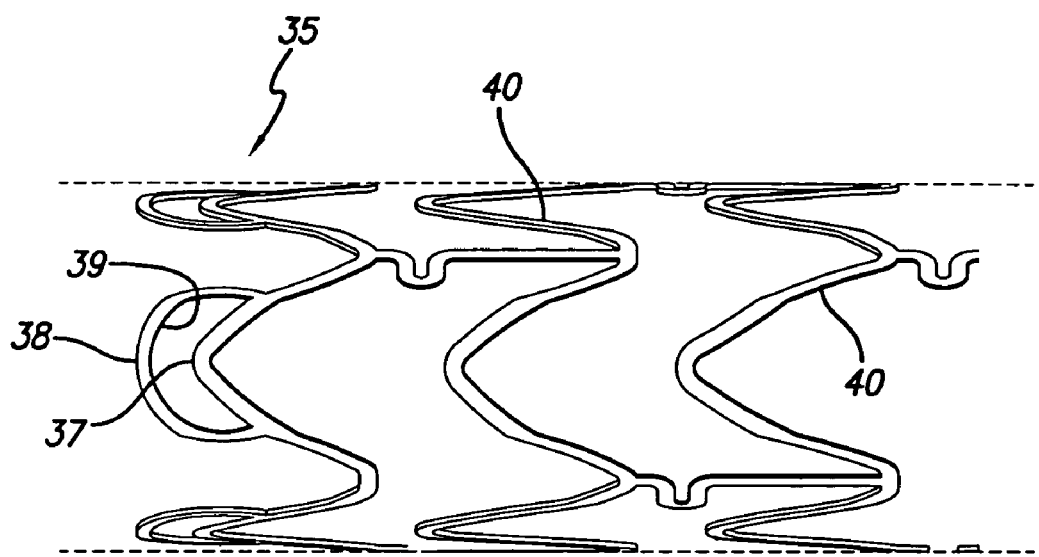
FIGS. 11 and 12 are partial plan views of a portion of the invention showing the end rings in the fully expanded configuration.
Figure 12:
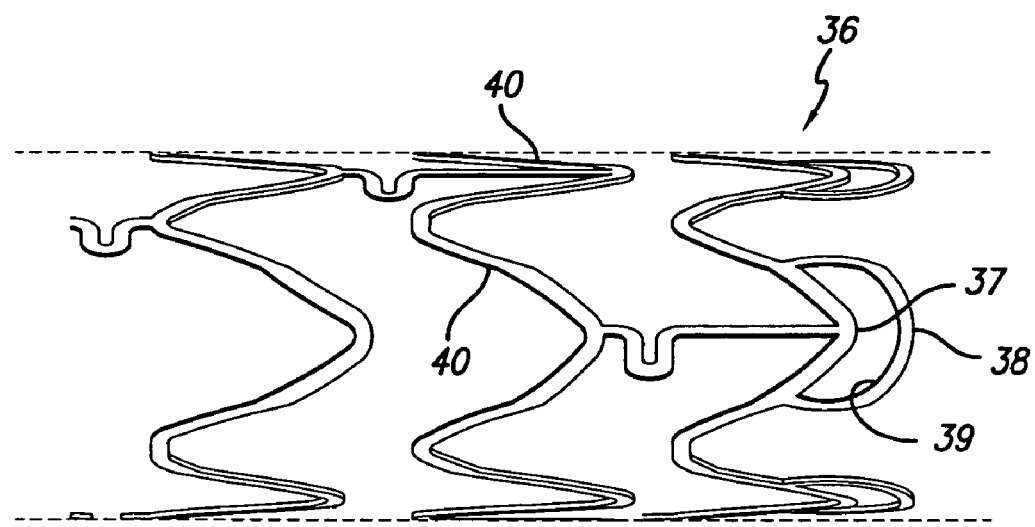

As illustrated in FIG. 10, the first peak 37 and the second peak 38, due to their radius of curvature, form the aperture 39, which can have any configuration, depending upon the configuration of the first and second peaks. For example, the second peaks can be semi-circular-shaped, oval-shaped, U-shaped, V-shaped, or have an irregular shaped curve (golf-club-shaped), and still function as described. As shown by the points depicted in FIG. 10, the path of the expansion of the first and second peaks is defined. Points P1 show the position of the first peak and the aperture when the stent is in the unexpanded state, and crimped on the balloon portion of the catheter. As the stent expands radially, first peak 37 spreads apart and expands radially and circumferentially so that the position P1 shifts to position P2 as shown. As that portion of the first peak shifts from points P1 to points P2, the spreading apart of the first peak acts as a lever to push second peak 38 longitudinally away from the first peak, and also helps to expand the second peak thereby increasing the size (area) of aperture 39. As a result of the lever action of the expansion of the first peak, the second peak is pushed along the longitudinal axis from the stent away from the first peak thereby extending the overall length of the stent. FIGS. 11 and 12 illustrate the proximal and distal portions of the stent respectively, and the end rings in particular. It can be seen that the end rings have extended longitudinally which counteracts the tendency of the stent to foreshorten as it is expanded. As long as the structure of the first peak is stiffer or more rigid than that of the second peak, the second peak can have virtually any shape and still extend longitudinally upon stent expansion.

In one embodiment, the circumferential or lateral length or dimension of the second peak 38, is greater than the distance between the two intersection points P1 as shown in FIG. 10. Thus, when the second peak expands the obliquely pointing strut portions of the second peak at points P1 and P2 become less inwardly pointing. In this way, when the stent expands the second peak will not be pulled back toward the stent in a longitudinal direction, but will instead be pushed outwardly away from the stent in a longitudinal direction.

Figure 13:
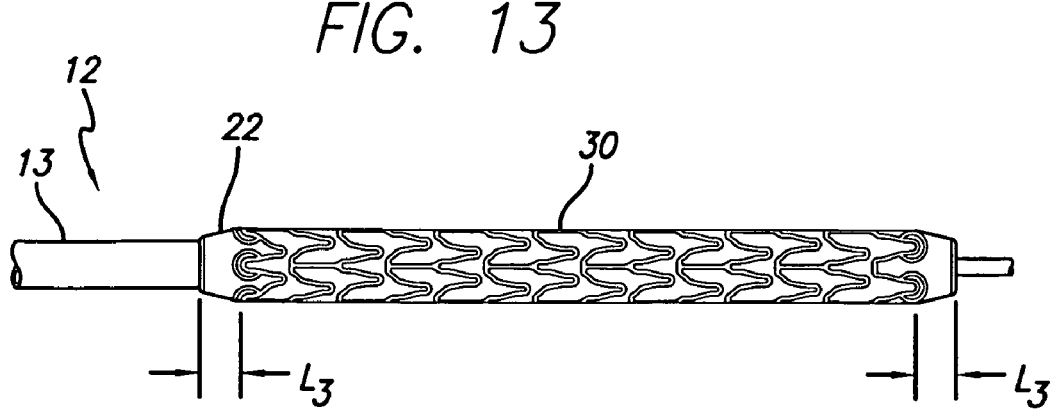
FIG. 13 is a plan view of the stent of the invention mounted on an expandable member and showing the stent-to-shoulder distance in the unexpanded configuration.
Figure 14:
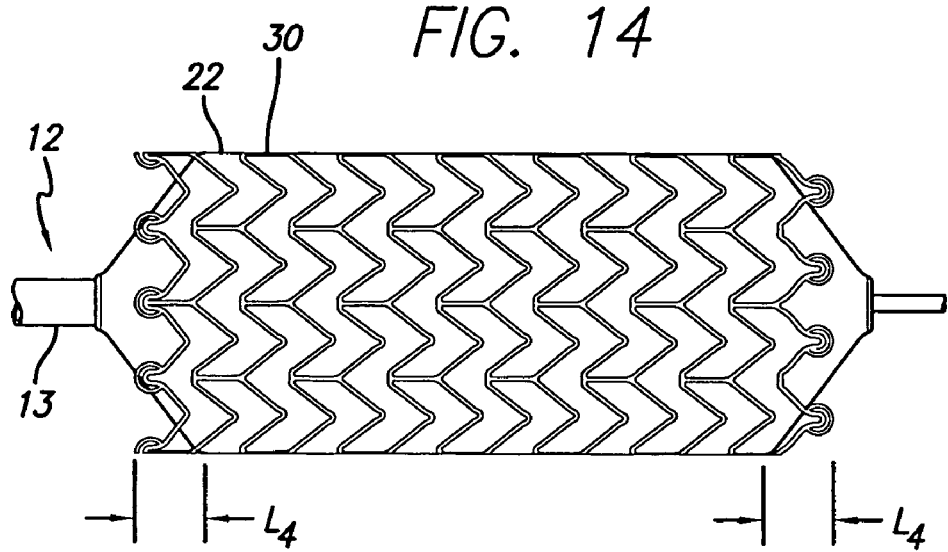
FIG. 14 is a plan view of the catheter assembly shown in FIG. 13 where the expandable member has been expanded thereby changing the stent-to-shoulder distance.

In order to illustrate the benefits of the present invention, as shown in FIGS. 13 and 14, stent 30 is mounted on the balloon portion 22 of catheter 13. The catheter assembly 12 can be any type of conventional catheter, such as a rapid exchange or over-the-wire catheter. As shown in FIG. 13, the stent-to-shoulder (STS) ratio L3 is an equal amount for both the proximal end and the distal end of the stent. While the length of stents vary greatly, as do the lengths of the working portions of the balloon, in one example the stent length before expansion was 20.3 mm and the stent length after expansion was 21.1 mm. The change in length of the stent of 0.8 mm was due entirely to the extension of the proximal end ring 36 and the distal end ring 35. Further, the STS for the distance L3 in FIG. 13, was 2.0 mm, while the STS of the distance L4, shown in FIG. 14, is −0.4 mm. The negative value means that the second peaks extend beyond the shoulder portion of the balloon and will extend into the aforementioned peri-stent area. Thus, if the stent is drug loaded, the drug applied to the second peak will treat the peri-stent region since the second peak has extended longitudinally past the shoulder portion of the balloon. Even if the stent is not treated with a drug, the support provided by the extended second peak in the peri-stent region should reduce the likelihood of development of restenosis in that area. The stent of the present invention also can be used to treat arteries having vulnerable plaque. The stent is placed in the artery to support and protect the fibrous cap covering the vulnerable plaque from rupturing.

As can be seen in FIGS. 6-8 undulating links 54 connect one cylindrical ring 31 to an adjacent cylindrical ring and contribute to the overall longitudinal flexibility to the stent due to their unique construction. The flexibility of the undulating links derives in part from curved portion 56 connected to straight portions 58 wherein the straight portions are substantially perpendicular to the longitudinal axis of the stent. Thus, as the stent is being delivered through a tortuous vessel, such as a coronary artery, the curved portions 56 and straight portions 58 of the undulating links will permit the stent to flex in the longitudinal direction which substantially enhances delivery of the stent to the target site. The number of bends and straight portions in a link can be increased or decreased from that shown, to achieve differing flexibility constructions. With the straight portions being substantially perpendicular to the stent longitudinal axis, the undulating link acts much like a hinge at the curved portion to provide flexibility. A straight link that is parallel to the stent axis typically is not flexible and does not add to the flexibility of the stent.

It is also a design feature that more or fewer undulating links 54 will be positioned between adjacent cylindrical rings 31. Further, in order to increase stent stability, straight links, in addition to undulating links, can be used to connect adjacent cylindrical rings. The straight links will provide stability and assist in preventing stent foreshortening, as do the undulating links. Further, the straight links may provide more rigidity in a localized area, such as at the stent ends, such that it may be desirable to incorporate more straight links between the cylindrical rings at the stent ends than in the center of the stent.

In one aspect of the invention, after stent 30 is implanted in a coronary artery, or other vessel, because of its novel design, the cylindrical rings 31 have the ability to flex radially as the vessel pulsates when blood pumps through it. Likewise, because of the novel and unique design of undulating links 54, as the vessel moves and pulsates from the pumping blood, the stent can flex longitudinally. The radial and longitudinal flexing of the stent reduces the likelihood that the stent will cause injury to the intima of a coronary artery, which also may have a tendency to reduce the likelihood of restenosis.

The stent of the present invention also can be used to treat arteries having vulnerable plaque. The stent is placed in the artery to support and protect the fibrous cap covering the vulnerable plaque from rupturing.

Figure 15:
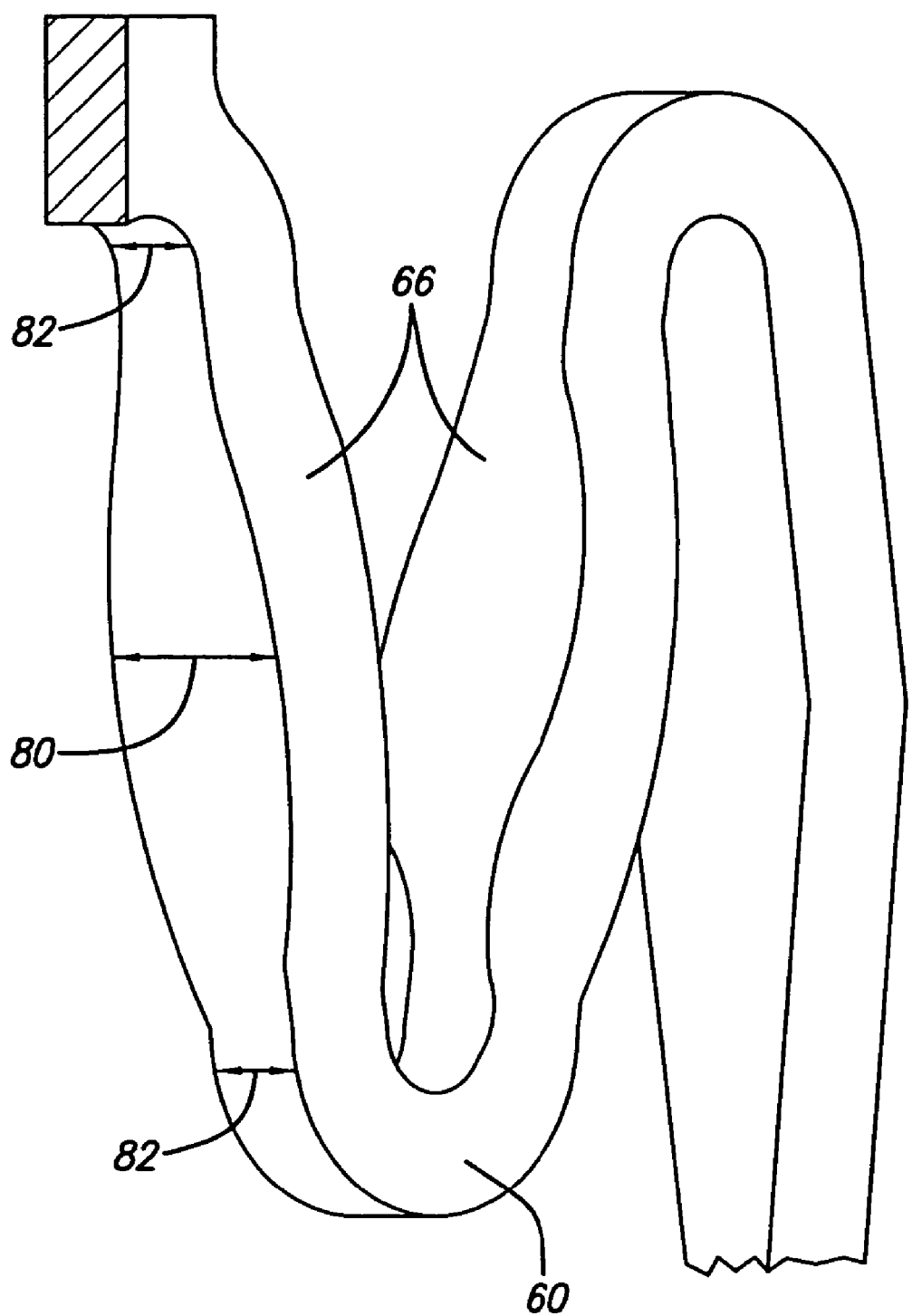
FIG. 15 is an enlarged partial perspective view of a portion of a peak and associated struts depicting variable thickness struts.

In another aspect of the invention, the stent 30 is formed so that the various struts of the cylindrical rings 31, all can be formed so that each has a variable thickness along the stent length. For example, the undulating link, and its associated arms may be thicker at one end than at the other end of the link. Further, first struts 66 and second struts 68 may vary in thickness (radial thickness) along their length in order to create variable flexibility in the rings. As shown in FIG. 15, peak 60 has first struts 66 that have radially thick portion 80 in the middle of the struts and radially thin portion 82 near the ends of the struts. As another example, the rings at, for example, the proximal end of the stent may be thicker radially than the rings in the center of the stent. A variable thickness stent that would benefit from the present invention is described and disclosed in U.S. Ser. No. 09/343,962 filed Jun. 30, 1999 and entitled VARIABLE THICKNESS STENT AND METHOD OF MANUFACTURE THEREOF, which is incorporated herein in its entirety by reference thereto. A variable thickness stent would benefit from the flexible nature of the present invention stent and still be crimped to a very low profile delivery diameter.

The stent 30 of the present invention can be mounted on a balloon catheter similar to that shown in the prior art device in FIG. 1. The stent is tightly compressed or crimped onto the balloon portion of the catheter and remains tightly crimped onto the balloon during delivery through the patient's vascular system. When the balloon is expanded, the stent expands radially outwardly into contact with the body lumen, for example, a coronary artery. When the balloon portion of the catheter is deflated, the catheter system is withdrawn from the patient and the stent remains implanted in the artery. Similarly, if the stent of the present invention is made from a self-expanding metal alloy, such as nickel-titanium or the like, the stent may be compressed or crimped onto a catheter and a sheath (not shown) is placed over the stent to hold it in place until the stent is ready to be implanted in the patient. Such sheaths are well known in the art. Further, such a self-expanding stent may be compressed or crimped to a delivery diameter and placed within a catheter. Once the stent has been positioned within the artery, it is pushed out of the catheter or the catheter is withdrawn proximally and the stent held in place until it exits the catheter and self-expands into contact with the wall of the artery. Balloon catheters and catheters for delivering self-expanding stents are well known in the art.

Examples of therapeutic drugs or pharmacologic compounds that may be loaded onto the stent pattern or into a polymeric coating on the stent, on a polymeric sleeve, or on individual filament strands on the stent, and delivered to the target site in the vasculature include taxol, aspirin, prostaglandins, and the like. Various therapeutic agents such as antithrombogenic or antiproliferative drugs are used to further control local thrombosis. Examples of therapeutic agents or drugs that are suitable for use in accordance with the present invention include 17-beta estradiol, sirolimus, everolimus, actinomycin D (ActD), taxol, paclitaxel, or derivatives and analogs thereof. Examples of agents include other antiproliferative substances as well as antineoplastic, antiinflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents include antiplatelets, anticoagulants, antifibrins, antiinflammatories, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B® (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from Hoffman-LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck), methotrexate, monoclonal antibodies (such as PDGF receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone.

The stent 30 of the present invention can be made in many ways. One method of making the stent is to cut a thin-walled tubular member, such as stainless steel tubing to remove portions of the tubing in the desired pattern for the stent, leaving relatively untouched the portions of the metallic tubing which are to form the stent. The stent also can be made from other metal alloys such as tantalum, nickel-titanium, cobalt-chromium, titanium, shape memory and superelastic alloys, and the nobel metals such as gold or platinum. In accordance with the invention, it is preferred to cut the tubing in the desired pattern by means of a machine-controlled laser as is well known in the art.

Direct laser cutting produces edges which are essentially perpendicular to the axis of the laser cutting beam, in contrast with chemical etching and the like which produce pattern edges which are angled. Hence, the laser cutting process essentially provides strut cross-sections, from cutto-cut, which are square or rectangular, rather than trapezoidal. The struts have generally perpendicular edges formed by the laser cut. The resulting stent structure provides superior performance.

Other methods of forming the stent of the present invention can be used, such as using different types of lasers; chemical etching; electric discharge machining; laser cutting a flat sheet and rolling it into a cylinder; and the like, all of which are well known in the art at this time.

The stent of the present invention also can be made from metal alloys other than stainless steel, such as shape memory alloys. Shape memory alloys are well known and include, but are not limited to, nickel-titanium and nickel-titanium-vanadium. Any of the shape memory alloys can be formed into a tube and laser cut in order to form the pattern of the stent of the present invention. As is well known, the shape memory alloys of the stent of the present invention can include the type having superelastic or thermoelastic martensitic transformation, or display stress-induced martensite. These types of alloys are well known in the art and need not be further described here.

Importantly, a stent formed of shape memory alloys, whether the thermoelastic or the stress-induced martensite-type, can be delivered using a balloon catheter of the type described herein, or be delivered via a catheter without a balloon or a sheath/catheter assembly.

The present invention can also include the stent being formed from materials other than the metallic materials previously described. For example, the rings can be formed from a metal alloy, while the links can be formed from a polymer that has sufficient column strength to space the rings, while maintaining flexural flexibility along the longitudinal axis of the stent. The metallic material forming the rings provides the necessary radial rigidity for delivery and after the stent has been implanted to hold open the body lumen, while the polymer links provide flexibility and have sufficient column strength to maintain the spacing of the rings. Further, the stent of the present invention can be formed entirely of a polymer, including the rings and links. The end rings would still function as previously described, wherein the second peak of the end rings would extend longitudinally upon expansion of the stent. Also, the polymer can be a biodegradable material that, over time, will degrade and be absorbed into the body lumen.

While the invention has been illustrated and described herein, in terms of its use as an intravascular stent, it will be apparent to those skilled in the art that the stent can be used in other body lumens. Further, particular sizes and dimensions, number of undulations or U-shaped portions per ring, materials used, and the like have been described herein and are provided as examples only. Other modifications and improvements may be made without departing from the scope of the invention.

What is claimed:

1. A flexible intravascular stent for use in a body lumen, comprising:
    a plurality of cylindrical rings aligned along a common longitudinal axis and interconnected to form a stent, each cylindrical ring having a first delivery diameter and a second implanted diameter;
    a distal end ring having a plurality of first peaks and a plurality of second peaks, the first peaks and second peaks defining an aperture therebetween; and
    a proximal end ring having a plurality of first peaks and a plurality of second peaks, the first peaks and second peaks defining an aperture therebetween;
    wherein said interconnection of said cylindrical rings and said arrangement of said first and second peaks cause said stent to increase in longitudinal length upon expansion from its delivery diameter to its implanted diameter.

2. The stent of claim 1, wherein the distal end ring and the proximal end ring have an unexpanded length L1 and an expanded length L2, wherein L2 is greater than L1.

3. The stent of claim 1, wherein the size of the apertures become larger when the stent expands.

4. The stent of claim 1, wherein the plurality of second peaks of the distal end ring extend longitudinally in a distal direction when the stent is expanded from the first delivery diameter to the second implanted diameter.

5. The stent of claim 1, wherein the plurality of second peaks of the proximal end ring extend longitudinally in the proximal direction when the stent is expanded from the first delivery diameter to the second implanted diameter.

6. The stent of claim 1, wherein at least one undulating link attaches each cylindrical ring to an adjacent cylindrical ring.

7. The stent of claim 6, wherein at least a portion of the undulating links has a variable thickness configuration.

8. The stent of claim 1, wherein the cylindrical rings are configured to provide flexibility to the stent.

9. The stent of claim 1, wherein the stent is formed from a tube.

10. The stent of claim 1, wherein the stent is formed from a flat sheet.

11. The stent of claim 1, wherein the stent is formed from a metal alloy.

12. The stent of claim 11, wherein the stent is formed from any of the group of metal alloys consisting of stainless steel, tantalum, nickel-titanium, cobalt-chromium and titanium.

13. The stent of claim 1, wherein the stent is formed from a shape memory alloy.

14. The stent of claim 13, wherein the stent is formed from the group of shape memory alloys consisting of nickel-titanium and nickel-titanium-vanadium.

15. The stent of claim 1, wherein the stent is formed from a superelastic or pseudoelastic metal alloy.

16. The stent of claim 15, wherein the stent is formed from the group of superelastic or pseudoelastic metal alloys consisting of nickel-titanium and nickel-titanium-vanadium.

17. The stent of claim 1, wherein at least a portion of the stent has a variable thickness configuration.

18. The stent of claim 1, wherein at least a portion of the first peaks has a variable thickness configuration.

19. The stent of claim 1, wherein at least a portion of the second peaks has a variable thickness configuration.

20. The stent of claim 1, wherein at least a portion of one cylindrical ring has a variable thickness configuration.

21. The stent of claim 1, wherein the first peaks have a first strut width and the second peaks have a second strut width, the first strut width being greater than the second strut width.

22. The stent of claim 1, wherein the first peaks and the second peaks have a uniform and equal strut width.

23. The stent of claim 1, wherein the stent has a therapeutic drug coating.

24. The stent of claim 1, wherein the first peaks and the second peaks have two intersection points P1, and a circumferential dimension of the second peak being greater than a distance between the points P1.

25. The stent of claim 1, wherein at least one link connects adjacent rings, the at least one link being attached to a distal end on one ring and a distal end on an adjacent ring.

26. The stent of claim 1, wherein the cylindrical rings have U-shaped undulations having an in-phase configuration.

27. A stent delivery catheter assembly for use in a body lumen, comprising:
  an elongated catheter having a proximal end and a distal end, and an expandable member near the distal end of the catheter;
  an intravascular stent mounted on the expandable member, the stent having a plurality of cylindrical rings aligned along a common longitudinal axis and interconnected to form the stent, each cylindrical ring having a first delivery diameter and second implanted diameter;
  a distal end ring having a plurality of first peaks and a plurality of second peaks, the first peaks and the second peaks defining an aperture;
  a proximal end ring having a plurality of first peaks and a plurality of second peaks, the first peaks and the second peaks defining an aperture;
  the expandable member having a shoulder, wherein the stent-to-shoulder distance in the unexpanded delivery diameter is L3, the stent-to-shoulder distance in the expanded and second implanted diameter is L4, wherein L3 is a positive number and L4 is a negative number.

28. The stent delivery catheter assembly of claim 27, wherein the end rings have a length L1 when the stent is in the first delivery diameter configuration, and a length L2 when the stent is in the second implanted diameter configuration, whereby L2 is greater than L1.

29. The stent delivery catheter assembly of claim 27, wherein the stent has a length in the first delivery diameter configuration and a length in the second implanted diameter configuration, the stent length in the second implanted diameter configuration being greater than the stent length in the first delivery diameter configuration.

30. The stent delivery catheter assembly of claim 27, wherein the plurality of second peaks of the distal end ring and the plurality of second peaks of the proximal end ring extend longitudinally when the stent expands from the first delivery diameter to the second implanted diameter.

* * * * *